(12) United States Patent
Hora et al.

(10) Patent No.: US 10,926,267 B2
(45) Date of Patent: Feb. 23, 2021

(54) METHOD AND SYSTEM FOR REDUCING THE UNFERMENTABLE SOLIDS CONTENT IN A PROTEIN PORTION AT THE BACK END OF A CORN DRY MILLING PROCESS

(71) Applicant: Fluid Quip Technologies, LLC, Springfield, OH (US)

(72) Inventors: Michael Hora, Marion, IA (US); John Kwik, Bellbrook, OH (US); Neal Jakel, Cedar Rapids, IA (US)

(73) Assignee: Fluid Quip Technologies, LLC, Springfield, OH (US)

( * ) Notice: Subject to any disclaimer, the term of this patent is extended or adjusted under 35 U.S.C. 154(b) by 0 days.

(21) Appl. No.: 16/199,486

(22) Filed: Nov. 26, 2018

(65) Prior Publication Data
US 2019/0160470 A1    May 30, 2019

Related U.S. Application Data

(60) Provisional application No. 62/599,846, filed on Dec. 18, 2017, provisional application No. 62/590,703, filed on Nov. 27, 2017.

(51) Int. Cl.
| | |
|---|---|
| *B02C 9/04* | (2006.01) |
| *A23K 10/38* | (2016.01) |
| *C11B 13/00* | (2006.01) |
| *C12P 7/20* | (2006.01) |
| *C13K 13/00* | (2006.01) |
| *C12P 7/08* | (2006.01) |
| *C13K 1/02* | (2006.01) |
| *A23K 20/147* | (2016.01) |
| *A23K 10/30* | (2016.01) |
| *A23J 1/12* | (2006.01) |
| *A23K 50/80* | (2016.01) |
| *A23K 50/40* | (2016.01) |
| *A23K 50/10* | (2016.01) |

(52) U.S. Cl.
CPC .............. *B02C 9/04* (2013.01); *A23J 1/12* (2013.01); *A23K 10/30* (2016.05); *A23K 10/38* (2016.05); *A23K 20/147* (2016.05); *A23K 50/10* (2016.05); *A23K 50/40* (2016.05); *A23K 50/80* (2016.05); *C11B 13/00* (2013.01); *C12P 7/08* (2013.01); *C12P 7/20* (2013.01); *C13K 1/02* (2013.01); *C13K 13/007* (2013.01)

(58) Field of Classification Search
CPC ........................................................ A23J 1/12
See application file for complete search history.

(56) References Cited

U.S. PATENT DOCUMENTS

| | | |
|---|---|---|
| 4,361,651 A | 11/1982 | Keim |
| 4,407,955 A | 10/1983 | Muller et al. |
| 4,624,805 A | 11/1986 | Lawhon |
| 5,066,498 A | 11/1991 | McCauley, III |
| 5,177,008 A | 1/1993 | Kampen |
| 5,250,182 A | 10/1993 | Bento et al. |
| 5,662,810 A | 9/1997 | Willgohs |
| 5,958,233 A | 9/1999 | Willgohs |
| 6,071,378 A | 6/2000 | Saito |
| 6,095,065 A | 8/2000 | Dietrich, Sr. |
| 6,509,180 B1 | 1/2003 | Verser et al. |
| 6,962,722 B2 | 11/2005 | Dawley et al. |
| 7,101,691 B2 | 9/2006 | Kinley et al. |
| 7,351,559 B2 | 4/2008 | Verser et al. |
| 7,494,675 B2 | 2/2009 | Abbas et al. |
| 7,601,858 B2 | 10/2009 | Cantrell et al. |
| 7,608,729 B2 | 10/2009 | Winsness et al. |
| 7,829,680 B1 | 11/2010 | Sander et al. |
| 8,008,516 B2 | 8/2011 | Cantrell et al. |
| 8,008,517 B2 | 8/2011 | Cantrell et al. |
| 8,103,385 B2 | 1/2012 | Macharia et al. |
| 8,168,037 B2 | 5/2012 | Winsness |
| 8,257,951 B2 | 9/2012 | Prevost et al. |
| 8,283,484 B2 | 10/2012 | Cantrell et al. |
| 8,679,353 B2 | 3/2014 | Winsness |
| 8,679,793 B2 | 3/2014 | Lewis |
| 8,722,911 B2 | 5/2014 | Bleyer et al. |
| 8,778,433 B2 | 7/2014 | Lee |
| 8,813,973 B2 | 8/2014 | Lee |
| 8,906,204 B2 | 12/2014 | Xu |
| 8,956,460 B2 | 2/2015 | Ahmed et al. |
| 8,986,551 B2 | 3/2015 | Kohl et al. |
| 9,029,126 B2 | 5/2015 | Bleyer et al. |
| 9,066,531 B2 | 6/2015 | Williams |
| 2003/0180415 A1 | 9/2003 | Stiefel et al. |
| 2004/0082044 A1 | 4/2004 | Prevost et al. |
| 2004/0087808 A1 | 5/2004 | Prevost et al. |

(Continued)

FOREIGN PATENT DOCUMENTS

| | | |
|---|---|---|
| CN | 1242879 C | 2/2006 |
| EP | 0395556 A1 | 10/1990 |

(Continued)

OTHER PUBLICATIONS

European Patent Office, Extended Search Report issued in EP 18208510.0 dated Mar. 22, 2019, 7 pages.

(Continued)

*Primary Examiner* — Bin Shen
(74) *Attorney, Agent, or Firm* — Wood Herron & Evans LLP

(57) ABSTRACT

A method and system for reducing the unfermentable solids content in a protein portion, via a counter current wash, at the back end of a corn dry milling process for making alcohol is disclosed. The method can include separating the whole stillage byproduct into an insoluble solids portion and a stillage (centrate) portion, which includes protein. Thereafter, the stillage portion can be separated into a water soluble solids portion and a protein portion. The protein portion may be mixed with clean water to wash and dilute the protein portion. The diluted protein portion may be dewatered to form a dewatered protein portion and a centrate. A portion of the centrate may be used as a protein counter current wash when the protein portion is being separated from the stillage portion. The protein counter current wash reduces the amount of unfermentable solids in the protein portion and the centrate.

8 Claims, 5 Drawing Sheets

(56) References Cited

U.S. PATENT DOCUMENTS

| | | |
|---|---|---|
| 2006/0006116 A1 | 1/2006 | Scheimann et al. |
| 2006/0041153 A1 | 2/2006 | Cantrell et al. |
| 2006/0057251 A1 | 3/2006 | Dawley et al. |
| 2006/0071378 A1 | 4/2006 | Brown |
| 2006/0091050 A1 | 5/2006 | Hwang |
| 2006/0173169 A1 | 8/2006 | Cheryan |
| 2006/0194296 A1 | 8/2006 | Hammond et al. |
| 2007/0039853 A1 | 2/2007 | Angulo Aramburu |
| 2007/0254089 A1 | 11/2007 | Hickey et al. |
| 2008/0026101 A1 | 1/2008 | Nickel et al. |
| 2008/0044547 A1 | 2/2008 | DeLine et al. |
| 2008/0095890 A1 | 4/2008 | Watson |
| 2008/0110577 A1 | 5/2008 | Winsness |
| 2008/0299632 A1 | 12/2008 | Winsness et al. |
| 2009/0029432 A1 | 1/2009 | Abbas et al. |
| 2009/0130257 A1 | 5/2009 | Abbas et al. |
| 2009/0250412 A1 | 10/2009 | Winsness et al. |
| 2009/0259060 A1 | 10/2009 | Cantrell et al. |
| 2010/0004474 A1 | 1/2010 | Cantrell et al. |
| 2010/0260918 A1 | 10/2010 | Wang et al. |
| 2012/0121565 A1 | 5/2012 | Williams |
| 2012/0205324 A1 | 8/2012 | Cantrell et al. |
| 2012/0244590 A1 | 9/2012 | Lee |
| 2012/0312905 A1 | 12/2012 | Claycamp |
| 2013/0164795 A1 | 6/2013 | Lowe et al. |
| 2014/0053829 A1 | 2/2014 | Lee |
| 2014/0142282 A1 | 5/2014 | Emanuele et al. |
| 2014/0147897 A1 | 5/2014 | Lee |
| 2014/0212543 A1 | 7/2014 | Lywood et al. |
| 2014/0220650 A1 | 8/2014 | Woods et al. |
| 2014/0242251 A1 | 8/2014 | Bootsma |
| 2014/0319066 A1 | 10/2014 | LoCascio et al. |
| 2014/0343259 A1 | 11/2014 | Bleyer et al. |
| 2015/0010975 A1 | 1/2015 | Burlew et al. |
| 2015/0056327 A1 | 2/2015 | Redford |
| 2015/0060259 A1 | 3/2015 | Xu |
| 2015/0064308 A1 | 3/2015 | Williams |
| 2015/0068058 A1 | 3/2015 | Buettner et al. |
| 2015/0080203 A1 | 3/2015 | Martyniuk |
| 2017/0114293 A1 | 4/2017 | Jakel et al. |

FOREIGN PATENT DOCUMENTS

| | | |
|---|---|---|
| EP | 0636692 A1 | 2/1995 |
| EP | 1988169 A1 | 11/2008 |
| WO | 8606098 A1 | 10/1986 |
| WO | 2010109203 A1 | 9/2010 |
| WO | 201414683 A1 | 1/2014 |
| WO | 201426947 A1 | 2/2014 |
| WO | 201433476 A2 | 3/2014 |
| WO | 2018226343 A1 | 12/2018 |
| WO | 2018231371 A1 | 12/2018 |

OTHER PUBLICATIONS

Zhang et al, "DDGS Production Technology, Research and Utilization Satus and Application in Livestock and Poultry Production,"Animals Breeding and Feed, Issue 10, pp. 38-42 (5 pages), 2008.

METHOD AND SYSTEM FOR REDUCING THE UNFERMENTABLE SOLIDS CONTENT IN A PROTEIN PORTION AT THE BACK END OF A CORN DRY MILLING PROCESS

TECHNICAL FIELD

The present invention relates generally to corn dry milling, and more specifically, to a method and system for reducing the unfermentable solids content in a protein portion at the back end of a corn (or similar carbohydrate-containing grain) dry milling process for making alcohol, such as ethanol, and/or other biofuels/biochemicals.

BACKGROUND

Wet mill corn processing plants convert corn grain into several different natural co-products, such as germ (for oil extraction), gluten feed (high fiber animal feed), gluten meal (high protein animal feed), and starch-based products, including ethanol, high fructose corn syrup, or food and industrial starch. Constructing wet-milling plants is complex and capital-intensive, and operating them is operationally complex and energy intensive.

Dry-mill ethanol plants alternatively have a much lower capital cost to build and lower operating cost to operate compared to a wet mill process. Dry milling plants generally convert corn into only two products, i.e., ethanol and distiller's grains with solubles. A typical corn dry milling process consists of four major steps: grain handling and milling, liquefaction and saccharification, fermentation and distillation, and co-product recovery. Grain handling and milling is the step in which the corn is brought into the plant and ground to promote better conversion of starch to glucose. Liquefaction is the step of converting solids such as starch to a flowable liquid producing oligosaccharides and saccharification is where the oligosaccharides are converted into single glucose molecules. Fermentation is the process of yeast or bacteria, or as clostridia, for example, converting glucose into a biofuel or a biochemical, such as ethanol. Distillation is the process of removing the biofuel or biochemical, such as ethanol, from the fermentation product. Co-product recovery is the step in which the corn by-products are dewatered and made ready for market. There are many known chemical and biological conversion processes known in the art that utilize yeast, bacteria, or the like to convert glucose to other biofuels and biochemical components like ethanol, for example.

The recovery of alcohol, e.g., butanol, ethanol (a natural co-product), etc., and other similar compounds, generally begins with the beer (spent fermentation broth) being sent to a distillation system. With distillation, ethanol is typically separated from the rest of the beer through a set of stepwise vaporizations and condensations. The beer less the alcohol extracted through distillation is known as whole stillage, which contains a slurry of the spent grains including corn protein, fiber, oil, minerals, sugars, and fermentation agent. This byproduct is too diluted to be of much value at this point and is further processed to provide the distiller's grains with solubles.

In typical processing, when the whole stillage leaves the distillation column, it is generally subjected at the back end of the process to a decanter centrifuge to separate insoluble solids or "wet cake", which includes mostly fiber, from the liquid or "thin stillage", which includes, e.g., protein, fine fiber, oil, and amino acids. The thin stillage may be separated into a water soluble solids portion and a protein portion. After separation, the water soluble solids portion moves to evaporators to boil away moisture, leaving a thick syrup that contains soluble (dissolved) solids. The concentrated syrup is typically mixed with the wet cake, and the mixture may be sold to beef and dairy feedlots as distillers wet grain with solubles (DWGS). Alternatively, the wet cake and concentrated syrup mixture may be dried in a drying process and sold as distillers dried grain with solubles (DDGS). The resulting DDGS generally has a crude protein content of about 29% and is a useful feed for cattle and other ruminants due to its protein and fiber content. The separated protein portion may be sent, via a protein stream, to be dewatered and dried to form a high protein corn meal product. The centrate from the dewatering of the protein stream can be recycled back to the front end of the corn dry milling process, i.e., at some point prior to fermentation, as backset. However, the recycled centrate can include an undersirable amount of unfermentable solids that can inhibit fermentation and/or decrease the amount of corn starch solids in the front end of the corn dry milling process.

It would be beneficial to provide a method and system that can reduce the amount of undersirable unfermentable solids in the separated protein portion thereby improving the throughput of the corn dry milling process and increasing overall protein yield gain, for example.

SUMMARY

The present invention relates to a method and system for reducing the unfermentable solids (e.g., carbohydrates, as well as minerals, fiber, or the like) content in protein portion, via a counter current wash, at the back end of a corn (or similar carbohydrate-containing grain) dry milling process for making alcohol, such as ethanol, and/or other biofuels/biochemical. The corn or other similar carbohydrate materials, such as wheat, barley, triticale, sorghum, tapioca, cassava, potato, rye, and other grains, include protein that can be eventually recovered therefrom as a product of the biofuel and/or biochemical dry milling process.

In one embodiment, a protein portion that is separated from a stillage stream subsequent to insoluble solids (wet cake) separation from the whole stillage may be sent, such as via a protein stream, to be optionally dewatered to form a dewatered protein portion and a resulting centrate. A portion of the centrate may be used as a protein counter current wash after the protein portion is separated from the stillage portion. The remainder of the centrate may be recycled back to the front end of the corn dry milling process, i.e., at some point prior to fermentation, as backset. Additionally the centrate may be further processed to yield, for example, a fertilizer or herbicide, or used as a raw material feed to produce a protein rich feed or food product.

In another embodiment, a protein portion that is separated from a stillage stream subsequent to insoluble solids (wet cake) separation from the whole stillage may be sent, such as via a protein stream, to be dewatered multiple times to form a dewatered protein portion and a resulting centrate. A portion of the centrate may be used as a protein counter current wash after the protein portion is separated from the from the stillage stream. The remainder of the centrate may be recycled back to the front end of the corn dry milling process, i.e., at some point prior to fermentation, as backset. Additionally the centrate may be further processed to yield, for example, a fertilizer or herbicide, used as a raw material feed to produce a protein rich feed or food product, or converted to energy.

In another embodiment, the remainder of the centrate can be further separated into a solids portion, including protein, and a liquid portion, including water soluble solids, with the liquid portion being utilized as backset and the solids portion being recycled back into the protein stream to provide a purer protein product and increase overall protein yield.

In still another embodiment, the protein portion that is separated from the stillage stream subsequent to insoluble solids (wet cake) separation from the whole stillage may be sent, such as via a protein stream, to be dewatered only once to form a dewatered protein portion and a resulting centrate. A portion of the centrate may be used as a protein counter current wash after the protein portion is separated from the stillage stream. And the remainder of the centrate can be further separated into a solids portion, including protein, and a liquid portion, including water soluble solids, with the liquid portion being utilized as backset and the solids portion being recycled back into the protein stream to provide a purer protein product and increase overall protein yield.

In yet another embodiment, a method for reducing an unfermentable solids content in a protein portion at a back end of a starch-containing grain dry milling process for making biofuel and/or a biochemical includes separating a whole stillage byproduct into an insoluble solids portion, which includes fiber, and a stillage portion, which includes protein. Next, counter current wash water that is received from a later step in the method is added to the stillage portion and the stillage portion is separated, via weights, into a water soluble solids portion and a protein portion, wherein the addition of the counter current wash water facilitates separation of a larger concentration of unfermentable solids into the water soluble solids portion. Then, the protein portion is recovered to define a high protein corn meal that includes at least 40 wt % protein on a dry basis. Recovering the protein portion can include dewatering or drying the protein portion, or dewatering followed by drying the protein portion to define the high protein corn meal.

In still another embodiment, a system for reducing an unfermentable solids content in a protein portion at a back end of a starch-containing grain dry milling process for making biofuel and/or a biochemical includes a first apparatus that receives a whole stillage byproduct produced via the starch-containing grain dry milling process, wherein the first apparatus separates the whole stillage byproduct into an insoluble solids portion, which includes fiber, and a stillage portion, which includes protein. A second apparatus is situated after the first apparatus and prior to any evaporator. The second apparatus is configured to receive the stillage portion from the first apparatus and counter current wash water from a later apparatus in the system and to separate the stillage portion, via weights, into a water soluble solids portion and a protein portion, wherein the addition of the counter current wash water facilitates separation of a larger concentration of unfermentable solids into the water soluble solids portion. A third apparatus is situated after the second apparatus and recovers the separated protein portion to define a high protein corn meal that includes at least 40 wt % protein on a dry basis. In one example, the first apparatus is a filtration centrifuge, a decanter centrifuge, a pressure screen, or a paddle screen, the second apparatus is a nozzle centrifuge or a cyclone apparatus, and the third apparatus is a decanter centrifuge or dryer.

In another embodiment, the system includes a fourth apparatus that is situated after the second apparatus and before the third apparatus. The fourth apparatus is configured to receive a mixture of the separated protein portion from the second apparatus and wash water and further configured to dewater the protein portion to provide a dewatered protein portion and a centrate portion that defines at least a portion of the counter current wash water. Here, the third apparatus is situated after the fourth apparatus and recovers the dewatered protein portion to define the high protein corn meal. In one example, the fourth apparatus is a decanter centrifuge and the third apparatus is a dryer.

The protein counter current wash reduces impurities, such as unfermentable solids (e.g., carbohydrates, as well as minerals, fiber, or the like), in the protein portion and the centrate. Due to the reduced unfermentable solids content in the recycled centrate, more corn may be processed in the corn dry milling process. That is, corn throughput in the corn dry milling process can be increased. Also, a purer protein product and overall protein yield gain can result.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

The present invention is directed to a method and system for reducing the unfermentable solids (e.g., carbohydrates) content in a protein portion, via a counter current wash, at the back end of a corn (or similar carbohydrate-containing grain) dry milling process for making a biofuel, e.g., alcohol, such as ethanol, or a biochemical, e.g., lactic acid.

Figure 1:
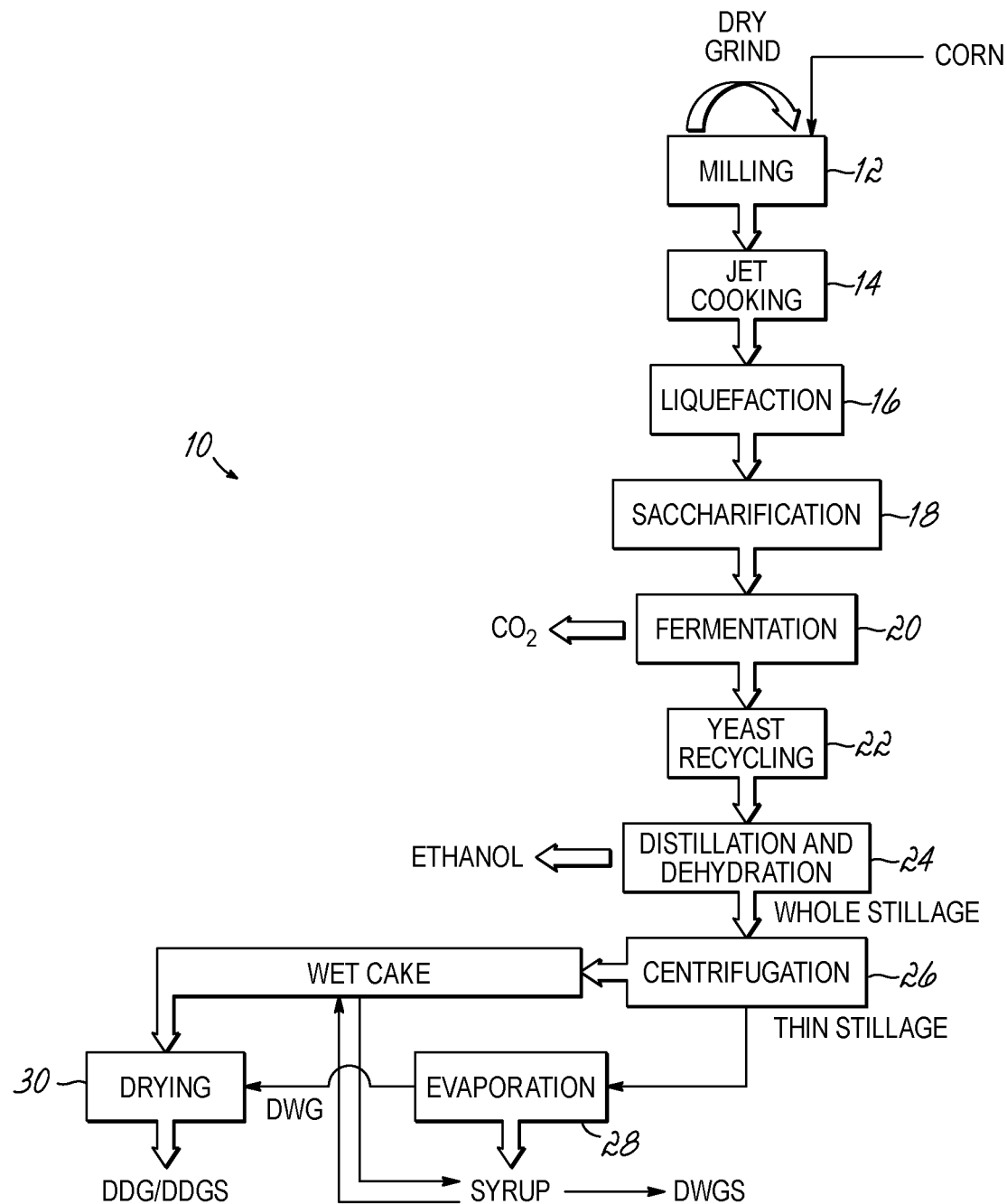
FIG. 1 is a flow diagram of a prior art dry milling process and system for producing ethanol and distiller's grains with solubles.

FIG. 1 is a flow diagram of a prior art corn dry milling process for producing alcohol, such process is fully discussed in U.S. Pat. No. 8,778,433, entitled "Methods for producing a high protein corn meal from a whole stillage byproduct". A significant portion of alcohol, e.g., ethanol, in the United States is produced from dry milling processes, which convert corn into two products, namely ethanol and distiller's grains with solubles. Although virtually any type and quality of grain, such as but not limited to sorghum, wheat, triticale, barley, rye, tapioca, cassava, potato, and other starch containing grains can be used to produce ethanol, the feedstock for this process is typically corn referred to as "No. 2 Yellow Dent Corn."

With specific reference to FIG. 1, a typical corn dry milling process 10 begins with a milling step 12 in which dried whole corn kernels are passed through hammer mills to grind them into meal or a fine powder. The ground meal is mixed with water to create a slurry, and a commercial enzyme such as alpha-amylase is added. This slurry is then typically pH adjusted and heated in a pressurized jet cooking process 14 to solubilize the starch in the ground meal. This is followed by a liquefaction step 16 at which point additional alpha-amylase may be added. The alpha-amylase hydrolyzes the gelatinized starch into maltodextrins and oligosaccharides to produce a liquefied mash or slurry.

This can be followed by separate saccharification and fermentation steps, 18 and 20, respectively, which may include a pH and temperature adjustment from the separate liquefaction step, although in most commercial dry milling ethanol processes, saccharification and fermentation occur simultaneously. In the saccharification step 18, the liquefied mash is cooled and a commercial enzyme, such as glucoamylase, is added to hydrolyze the maltodextrins and short-chained oligosaccharides into single glucose sugar molecules. In the fermentation step 20, a common strain of yeast (Saccharomyces cerevisae) is added to metabolize the glucose sugars into ethanol and $CO_2$. Other fermentation agents such as bacteria and clustridia can be utilized. Upon completion, the fermentation mash ("beer") will contain about 17% to 18% ethanol (volume/volume basis), plus soluble and insoluble solids from all the remaining grain components, including fiber, protein, minerals, and oil, for example. Yeast can optionally be recycled in a yeast recycling step 22. In some instances, the $CO_2$ is recovered and sold as a commodity product.

Subsequent to the fermentation step 20 is a distillation and dehydration step 24 in which the beer is pumped into distillation columns where it is boiled to vaporize the ethanol. The ethanol vapor after exiting the top of the distillation column is condensed and liquid alcohol (in this instance, ethanol) is about 95% purity (190 proof). The 190 proof ethanol can then go through a molecular sieve dehydration column or a membrane separation unit or similar dehydration system, which removes the remaining residual water from the ethanol, to yield a final product of essentially 100% ethanol (199.5 proof).

Finally, at the back end, a centrifugation step 26 involves centrifuging, via a decanter centrifuge, the residuals or whole stillage leftover from distillation so as to separate the insoluble solids portion or "wet cake", which includes fiber, from the liquid portion or "thin stillage" portion, which includes protein, amino acids, oil, fine fiber, etc. Next, the thin stillage portion enters evaporators in an evaporation step 28 in order to boil away moisture thereby leaving a thick syrup, which contains the soluble (dissolved) solids as well as protein and oil. This concentrated syrup is typically referred to as corn condensed distillers soluble and is mixed with the centrifuged wet cake then sold to beef and dairy feedlots as distillers wet grain with solubles (DWGS). The wet cake and concentrated syrup mixture may be further dried in a drying step 30 and sold as distillers dried grain with solubles (DDGS) to dairy and beef feedlots and/or the monogastric markets. The distiller's grains with solubles co-product provides a critical secondary revenue stream that offsets a portion of the overall ethanol production cost.

Figure 2:
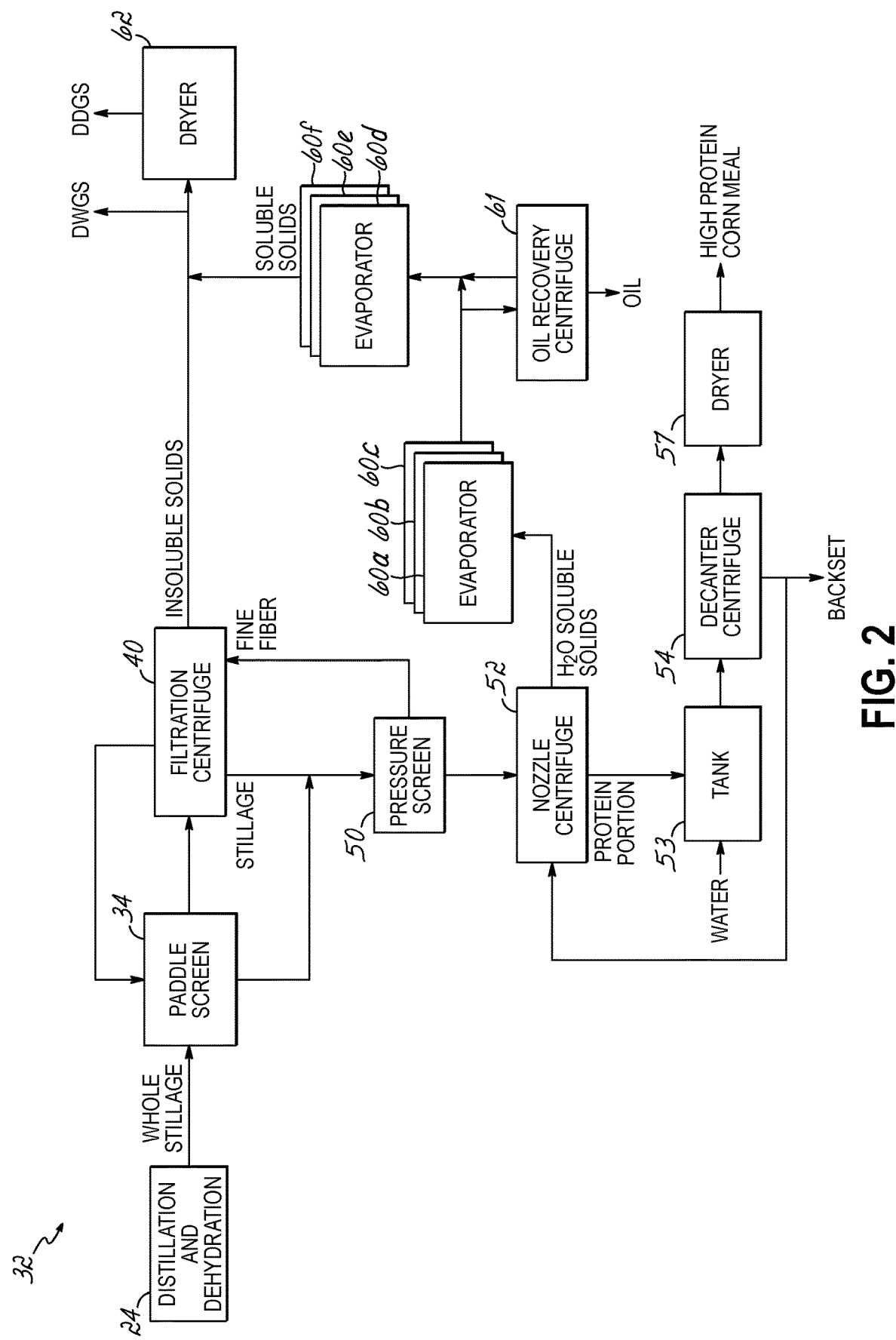
FIG. 2 is a flow diagram of a method and system for reducing the unfermentable solids content in a protein portion in a corn dry milling process for making alcohol in accordance with an embodiment of the invention.

In accordance with the present invention, FIG. 2 schematically illustrates an embodiment of a method and system, collectively numeral 32, for reducing the unfermentable solids (e.g., carbohydrates) content in a protein portion, via a back end counter current wash, with such protein initially separated with the stillage stream (centrate) from the whole stillage byproduct produced in a typical corn dry-milling process 10, like that just described in FIG. 1. While a typical whole stillage byproduct is utilized here, it should be understood that the whole stillage from any corn (or similar carbohydrate-containing grain) dry milling process may be utilized with the same or similar results. Again, the whole stillage byproduct contains a slurry of soluble and insoluble solids, i.e., the spent grains from the distillation and dehydration step 24, which can include amino acids, protein, fiber, minerals, and free oil, for example, that can be processed in accordance with embodiments of this invention.

With continuing reference to FIG. 2, the whole stillage byproduct can be piped from the typical corn dry milling distillation and dehydration step 24 and subjected to an optional paddle screen 34. The optional paddle screen 34 is situated before a filtration centrifuge 40, which is further discussed below, so as to aid ultimately in separation of the insoluble solids portion, e.g., fiber, from the resulting stillage portion by initially filtering out desirable amounts of water, amino acids, protein, and, incidentally, small fiber fines from the whole stillage byproduct. This initial screening can help reduce the resulting load on the subsequent filtration centrifuge 40. The resulting thrus (centrate) from the paddle screen 34 eventually joins with the stillage underflow (centrate) from the filtration centrifuge 40, as will be discussed in greater detail below.

To filter the whole stillage byproduct, the optional paddle screen 34 can include screen openings of no greater than about 500 microns. In another example, the paddle screen 34 can include openings therein of no greater than about 400 microns. In yet another example, the openings therein are no greater than about 300 microns. In yet another example, the paddle screen 34 can include openings therein of no greater than about 150 microns and yet another example, the paddle screen 34 can include openings therein of no greater than about 50 microns. It should be understood that these values are exemplary and that those of ordinary skill in the art will recognize how to determine the size of the openings to achieve the desired filtration. In one example, the optional paddle screen 34 is a standard type paddle screen as is known in the art. One such suitable paddle screen 34 is the FQ-PS32 available from Fluid-Quip, Inc. of Springfield, Ohio. It should be understood that the optional paddle screen 34 may be replaced with other types of pre-concentration devices, e.g., a standard pressure screen, conic centrifuge, cyclone, or hydroclone, which can perform the desired filtration or preconcentration function. One such suitable pressure screen is the PS-Triple available from Fluid-Quip, Inc. of Springfield, Ohio. In addition, although a single paddle screen 34 is depicted, it should be understood that a plurality of screens 34 may be situated in-line, either in series or in parallel, and utilized for filtering the whole stillage byproduct.

The whole stillage from the distillation and dehydration step 24, if the optional paddle screen 34 is not present, or the cake (solids) from the optional paddle screen 34 is sent to the filtration centrifuge 40 whereat the whole stillage byproduct or cake is separated into the insoluble solids portion, which includes fiber, and the stillage portion (centrate), which includes amino acids, protein, free oil, etc. One such suitable filtration centrifuge is described in Lee et al., U.S. Pat. No. 8,813,973 entitled "Apparatus and Method for Filtering a Material from a Liquid Medium", the contents of which are expressly incorporated by reference herein in its entirety. The filtration centrifuge 40 may be configured to perform both the initial filtering (sometimes referred to as a pre-concentration) of the whole stillage byproduct and washing of the fiber so as to clean the fiber and remove the amino acids, protein, free oil, and other components that remain associated with the fiber after the initial filtration or pre-concentration.

With respect to the filtration centrifuge 40, the washing of the fiber may include a washing cycle, wherein the fiber is mixed and rinsed in wash water, followed by a de-watering cycle, wherein the wash water is separated from the fiber. The washing of the fiber may include multiple rinsing/de-watering cycles. Additionally, a counter current washing technique may be employed to save wash water usage. After washing the fiber, but before the fiber exits the centrifuge, the fiber may go through an enhanced de-watering stage, a compaction stage, and/or an air dry stage to further de-water or dry the fiber. This may reduce the dryer capacity or eliminate the dryer altogether. Eventually, the washed and filtered fiber exits the filtration centrifuge 40 so that the fiber can be further processed, as discussed further below, including dried, to result in a desired product, such as DWG(S) or DDG(S), which can be marketed or sold as is. In one example, the fiber can be transported to a remote site for further processing. Moreover, any separated out portion of slurry from the fiber, e.g., water, amino acids, protein, free oil, wash water, etc., which occurs via screening, is collected to define the stillage (centrate), then transported and further processed as described below. Optionally, a portion of the slurry and/or wash water may be piped back to the optional paddle screen 34 for further reprocessing. The filtration centrifuge 40 may provide the filtered material at a water concentration of between about 55% and about 75% water, which is a significant reduction compared to conventional filtration systems.

With continuing reference to FIG. 2, although a single filtration centrifuge 40 is depicted, it should be understood that a plurality of filtration centrifuges 40, either in parallel or series, may be situated in-line and utilized for separating the whole stillage byproduct into its insoluble solids portion (fiber) and stillage (centrate) portion. And in an alternate embodiment, it is contemplated that the filtration centrifuge 40 can be replaced by a standard pressure screen, decanter centrifuge, a paddle screen, or other like devices as are known in the art to separate the whole stillage byproduct into the insoluble solids portion and stillage (centrate) portion. One such suitable pressure screen is the PS-Triple available from Fluid-Quip, Inc. of Springfield, Ohio. One such suitable decanter centrifuge is the NX-944HS available from Alfa Laval of Lund, Sweden. And one such suitable paddle screen is the FQ-PS32 available from Fluid-Quip, Inc. of Springfield, Ohio. To further enhance the separation of non-protein components from the remaining kernel components, a flocculent can optionally be added to the whole stillage prior to a first separation step. A flocculent may help bind fiber and other kernel components together, making separation of those particles more efficient, thus resulting in improved protein recovery downstream.

As further shown in FIG. 2, the centrate (underflow) from the filtration centrifuge 40 is piped to join up with the thrus (centrate) from the optional paddle screen 34 prior to or at an optional standard pressure screen 50, as is known in the art, to further aid in separation of any fine fiber from the stillage (centrate) portion. If the optional paddle screen 34 is not present, the stillage underflow from the filtration centrifuge 40 is sent directly to optional pressure screen 50.

Prior to being subjected to the optional pressure screen 50, the stillage can include protein contained within the kernel of corn and protein from the fermentation agent. The protein content within this stream ranges from about 24.8% to 33.2% and solids content within this stream ranges from 5% to 15%.

Fiber having a size less than that of the screen of the filtration centrifuge 40 and/or optional paddle screen 34 may pass through and to subsequent steps of the corn dry milling process. At the pressure screen 50, the separated fine fiber can be separated from the stillage and piped back to the filtration centrifuge 40 or similar unit operations whereat the fine fiber may be filtered out to be further processed. One such suitable pressure screen 50 is the PS-Triple available from Fluid-Quip, Inc. of Springfield, Ohio. In an alternate embodiment, the optional pressure screen 50 may be replaced with a standard paddle screen or decanter centrifuge, as are mentioned above, or other like device, such as a filtration centrifuge, to aid in separation of the fine fiber from the stillage portion. In addition, although a single pressure screen 50 is depicted, it should be understood that a plurality of pressure screens 50, either in parallel or series, may be situated in-line and utilized for filtering the stillage underflow.

After the optional pressure screen 50, the remaining stillage portion can include a total protein content, as measured in a spin tube, of about 10 ml/50 ml of liquid sample. Additional protein that is water soluble will be in the supernate of the spun sample (water portion on top of the solid portion of the spun sample). The amount of protein in the spun sample can vary due to a number of factors; the value here represents an average. The protein content in the spun sample may be smaller or larger depending on upstream process variations and initial corn kernel protein content. The protein content in a 50 ml spin tube can have a range from about 5 ml up to 25 ml.

The remaining stillage portion from the optional pressure screen 50 is piped and subjected to a nozzle centrifuge 52, as is known in the art, to separate the stillage portion into a protein portion and a water soluble solids portion. Alternatively, if the optional pressure screen 50 is not present, the centrate can be sent directly to the nozzle centrifuge 52. The temperature of the stillage (centrate) portion entering the nozzle centrifuge 52 may be in a range of from 170° F. to 190° F. In another example, the temperature may be in a range from about 170° F. to 185° F. In yet another example, the temperature may be in a range from about 170° F. to 180° F. In another example, the temperature may be in a range from about 180° F. to 185° F. The nozzle centrifuge 52 can be provided with washing capabilities so that a protein counter current wash, along with the stillage portion, can be supplied to the nozzle centrifuge 52. As described below, the protein counter current wash can include a portion of the centrate from the subsequent dewatering of the separated protein portion at decanter centrifuge 54. Thus, the water in the protein counter current wash has already undergone a first wash, as further discussed below. In one embodiment, the protein counter current wash may include a dry solids content of about 2 to 8%. In another example, the protein counter current wash may include a dry solids content of about 2 to 6%. In yet another example, the protein counter current wash may include a dry solids content of about 2 to 4%. In another example, the protein counter current wash may include a dry solids content of about 3 to 5%. In yet another example, the protein counter current wash may include a dry solids content of about 4 to 6%. It should be understood by one skilled in the art that there are many upstream process conditions that can vary the final counter current wash solids and that the ranges provided are exemplary and not absolute values.

At the nozzle centrifuge 52, the protein counter current wash allows for easier separation of the stilage stream into the protein portion and the water soluble solids portion, which includes a larger concentration of unfermentable solids due to the counter current wash. In particular, the heavier protein portion separates from the lighter water soluble solids portion and is removed as the underflow whereas the lighter water soluble solids portion, which includes free oil as well as unfermentable solids (e.g., carbohydrates), can be removed as the overflow. The protein counter current wash reduces the amount of unfermentable solids from the resulting protein portion compared to using water, e.g, "clean" water, that has not previously undergone a wash (e.g., cook water or condensate). The protein counter current wash may also increase the amount of protein separated from the stilage portion into the protein portion. In other words, more unfermentable solids, such as carbohydrates (e.g., glycerol, oligosaccharides, polysaccharides, starch, as well as fine fiber), are separated from the protein portion and exit the nozzle centrifuge 52 in the water soluble solids portion. In one embodiment, the nozzle centrifuge 52 may operate at about 2900 RPM. In another example, the nozzle centrifuge 52 may operate at about 2600 to 3300 RPM. It should noted that different equipment and different equipment size have different RPM ranges and this information is only for exemplary purposes. One such suitable nozzle centrifuge 52 is the FQC-950 available from Fluid-Quip, Inc. of Springfield, Ohio. In an alternate embodiment, the nozzle centrifuge 52 can be replaced with a standard cyclone apparatus or other like device, as are known in the art, to separate the stilage portion into the underflow protein portion and overflow water soluble solids portion. One such suitable cyclone apparatus is the RM-12-688 available from Fluid-Quip, Inc. of Springfield, Ohio. In addition, although a single nozzle centrifuge 52 is depicted, it should be understood that a plurality of nozzle centrifuges 52, either in parallel or series, may be situated in-line and utilized here.

The underflow protein portion from the nozzle centrifuge 52 may be transported to a storage tank 53 and mixed with water, e.g., "clean" water/cook water or condensate, to further dilute the separated protein portion. The addition of clean water (e.g., cook water) before the decanter centrifuge 54 at tank 53 acts as a wash and occurs after the protein counter current wash that occurs at the nozzle centrifuge 52. In one embodiment, the added cook water can include a dry solids content of about 2 to 8%. In another example, the added cook water can include a dry solids content of about 2 to 4%. In another example, the added cook water can include a dry solids content of about 3 to 5%. In another example, the added cook water can include a dry solids content of about 4 to 6%.

The diluted protein portion from the tank 53 can be sent to decanter centrifuge 54 whereat the protein portion is dewatered to provide a dewatered protein portion. The additional cook water added to the underflow protein portion at tank 53 aids in further reducing the unfermentable solids content in the dewatered protein portion that exits the decanter centrifuge 54. The dry solids content of the dewatered protein portion may be, for example, in a range of from about 18 to 60%. In another example, the dry solids content of the dewatered protein portion is in a range of from about 30 to 60%. In another example, the dry solids content of the dewatered protein portion is in a range of from about 19 to 30%. In yet another example, the dry solids content of the dewatered protein portion is in a range of from about 18 to 35%, 23 to 33%, or 25 to 27%. In yet another example, the dry solids content of the dewatered protein portion is in a range of from about 19 to 22%. The decanter centrifuge 54 is standard and known in the art. The decanter centrifuge 54 may operate at about 2600 to 3300 RPM. In another example, the range can be 2950 to 3100 RPM. In another example, the range can be 2950 to 3100 RPM. In yet another example, the range can be 2700 to 2950 RPM. In yet another example, the decanter centrifuge 54 may operate at about 3050 RPM. It should noted that different equipment and different equipment size have different RPM ranges and this information is only for exemplary purposes. One such suitable decanter centrifuge 54 is the NX-944HS available One such suitable decanter centrifuge 54 is the NX-944HS available from Alfa Laval of Lund, Sweden. In addition, although a single decanter centrifuge 54 is depicted, it should be understood that a plurality of decanter centrifuges 54 may be situated in-line, either in series or parallel, and utilized here. In an alternate embodiment, the decanter centrifuge 54 may be replaced with a standard filter press or rotary vacuum, or other like device, as are known in the art, to dewater the stilage portion.

As described above, at least a portion of the centrate from the decanter centrifuge 54 can be recycled back to the nozzle centrifuge 52 to act as the protein counter current wash. The remainder of the centrate from the decanter centrifuge 54 may be recycled back to the front end as backset, for example, to the slurry prior to the jet cooking process 14, to liquefaction step 16, or to the fermentation step 20 for reuse in the dry milling process. As a result of the protein counter current wash, the unfermentable solids content in the centrate is also reduced such that fewer unfermentable solids get recycled back into the dry milling process. The centrate may have a dry solids content of about 2.0% to 6.0% compared to a content of about 6.5% in a process without the protein counter current wash. In another example, centrate may have a dry solids content of about 5.9%. This reduction in unfermentable solids in the centrate that is recycled back to the front end of the dry milling process may allow for more corn, or another grain, to be processed at one time. In other words, production throughput can increase as a result of the protein counter current wash. Additional benefits of the protein counter current wash include improved capture efficiency of the nozzle centrifuge 52 and the decanter centrifuge 54 as well as the flexibility to fine tune the protein purity by adjusting the amount of water added to the protein portion before entering the decanter centrifuge 54. Also, a purer protein product and overall protein yield gain can result.

The dewatered protein portion from the decanter centrifuge 54 can be further optionally dried, such as by being sent to a dryer 57, e.g., a spray dryer, ring dryer, flash dryer, compression dryer, or a crystallizer, as is known in the art. In another embodiment, the dewatered protein portion can be subjected to vacuum filtration or other dewatering and drying methods, as are known in the art. The final dried protein portion or product defines a high protein corn meal that may be sold at a much higher price per ton than DDGS or DWGS.

Returning now to the separated water soluble solids portion or filtrate from the nozzle centrifuge 52, which includes an increased unfermentable solids content, free oil as well as minerals, sugar and soluble proteins, the separated water soluble solids portion may be recycled back, for example, to the liquefaction step 16 or the fermentation step 20 for reuse in the dry milling process. Additionally or alternatively, as shown in FIG. 2, the water soluble solids portion can be piped from the nozzle centrifuge 52 and subjected to a set of three evaporators 60a, 60b, and 60c, as are known in the art, to begin separating the soluble solids from the water soluble solids portion. The evaporators 60a-c evaporate the liquid portion of the water soluble solids portion. Thereafter, the water soluble solids portion can be piped and subjected to an optional oil recovery centrifuge 61, as is known in the art, so that oil can be removed therefrom. One such suitable oil recovery centrifuge 261 is the ORPX 617 available from Alfa Laval of Lund, Sweden. In one example, the final recovered oil product can include between about 30 wt % to about 60 wt % of the total corn oil in the corn. In comparison to typical oil recovery in a standard dry milling process, oil recovery centrifuge 61 can function at a higher capacity because the water soluble solids portion, which is subjected to the oil recovery centrifuge 61, includes less liquid and less protein and fiber than normal.

The remainder of the water soluble solids portion can be piped and subjected to another set of three evaporators 60d, 60e, and 60f whereat the liquid portion is further evaporated from the water soluble solids portion to ultimately yield a soluble solids portion. While the water soluble solids portion is subjected to two sets of three evaporators 60a-c, 60d-f, it should be understood that the number of evaporators and sets thereof can be varied, i.e., can be more or less, from that shown depending on the particular application and result desired. Additionally, this soluble solids stream can be further processed as a raw material feed source, such as for a bio-digester to produce biofuels and/or biochemicals, an algae feed source, or further processed via fermentation, for example, to yield a high protein nutrient feed.

The resulting soluble solids portion may be combined with the insoluble solids portion, e.g., fiber, received from the filtration centrifuge 40 to provide distillers wet grains with soluble (DWGS), which may be further dried by a drier 62, as is known in the art, to provide distillers dry grains with solubles (DDGS), both of which can be sold to dairy or beef feedlots, monogastric markets for monogastric animals, or as pet food or aquaculture. In another example, the soluble solids portion may be used as a natural fertilizer. In another example, the soluble solids portion may be used as a raw material feed source for conversion to simple sugar, which can be further converted to biofuel or used in other biochemical processes.

Accordingly, in this dry-milling process, neither the DDGS nor DWGS receive the typical concentrated syrup from the evaporators 60. And, despite the lower protein content, the DDGS and DWGS may still be sold to beef and dairy feedlots as cattle feed or other animal feed markets.

Figure 3:
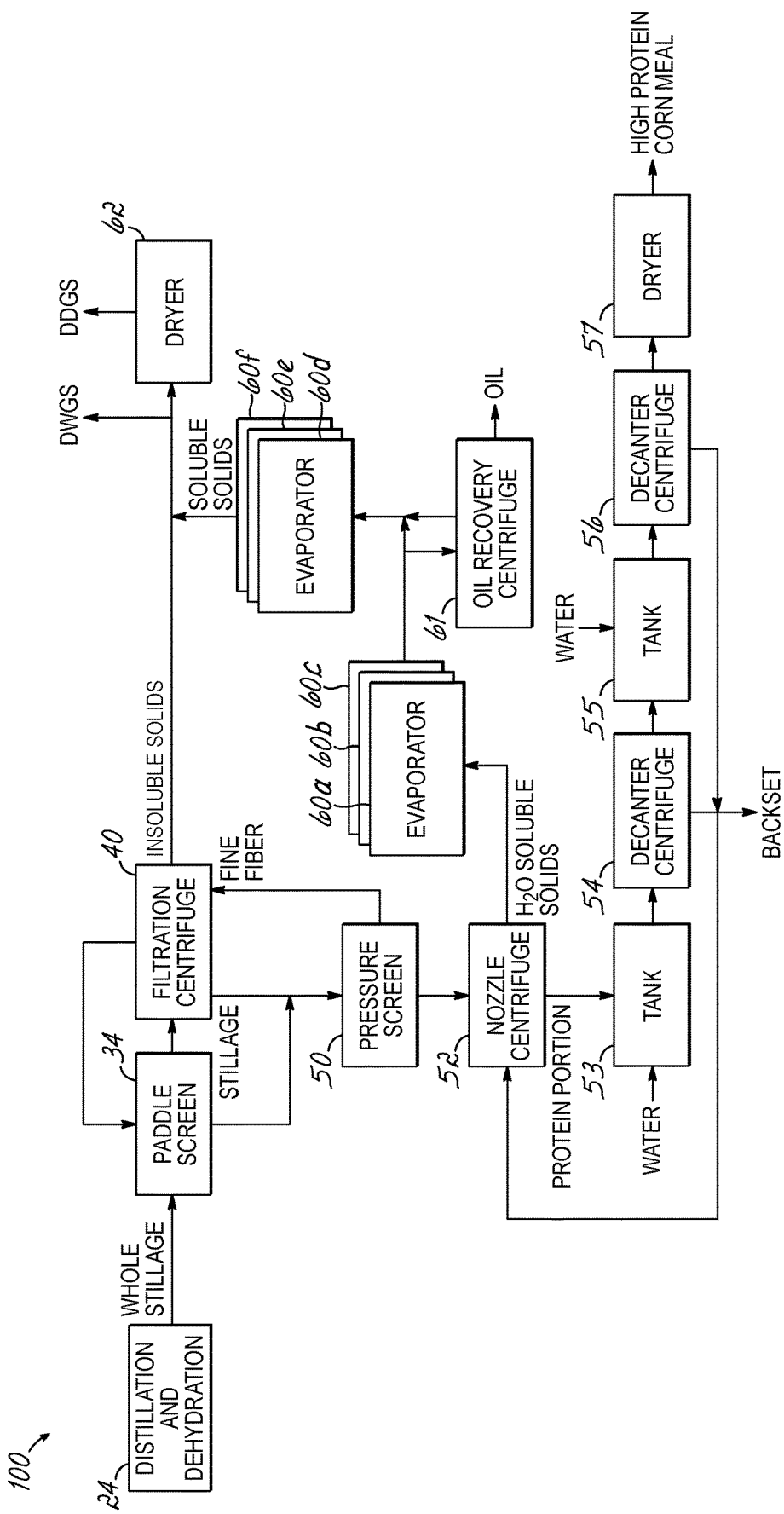
FIG. 3 is a flow diagram of a method and system for reducing the unfermentable solids content in a protein portion in a corn dry milling process for making alcohol and/or other biofuels/biochemicals in accordance with another embodiment of the invention.

In accordance with another embodiment of the invention, FIG. 3 schematically illustrates a method and system, collectively numeral 100, for reducing the unfermentable solids (e.g., carbohydrates) content in a protein portion, via a back end counter current wash, with such protein initially separated with the stillage (centrate) from the whole stillage byproduct produced in a typical corn dry-milling process 10, like that described in FIG. 1. Again, while a typical whole stillage byproduct is utilized here, it should be understood that the whole stillage from any corn (or similar carbohydrate-containing grain) dry milling process may be utilized with the same or similar results.

FIG. 3 is similar to the embodiment of FIG. 2, with the exception that there is an additional tank 55 and decanter centrifuge 56 after the initial tank 53 and decanter centrifuge 54 that follows nozzle centrifuge 52 discussed above with respect to FIG. 2. The protein counter current wash can include a portion of the centrate from the subsequent dewatering of the separated protein portion at decanter centrifuges 54 and 56, as discussed below.

In particular and with further reference to FIG. 3, the dewatered protein portion from the decanter centrifuge 54 may be transported to another storage tank 55 and mixed with water, e.g., "clean" water/cook water or condensate, to further dilute the dewatered protein portion, as above discussed with respect to the separated protein portion. The addition of clean water (e.g., cook water) at storage tank 54 acts as another wash. In one embodiment, the added cook water can include a dry solids content of about 2 to 8%. In another example, the added cook water can include a dry solids content of about 2 to 4%. In another example, the added cook water can include a dry solids content of about 3 to 5%. In another example, the added cook water can include a dry solids content of about 4 to 6%.

The diluted protein portion from the tank 55 can be sent to another decanter centrifuge 56 whereat the protein portion is further dewatered to again provide a dewatered protein portion. The additional cook water added to the dewatered protein portion at tank 55 aids in further reducing the unfermentable solids content in the dewatered protein portion that exits the decanter centrifuge 56. The dry solids content of the resulting dewatered protein portion after the decanter centrifuge 56 may be, for example, in a range of from about 18 to 60%. In another example, the dry solids content of the dewatered protein portion is in a range of from about 30 to 60%. In another example, the dry solids content of the dewatered protein portion is in a range of from about 19 to 30%. In yet another example, the dry solids content of the dewatered protein portion is in a range of from about 18 to 35%, 23 to 33%, or 25 to 27%. In yet another example, the dry solids content of the dewatered protein portion is in a range of from about 19 to 22%. The decanter centrifuge 56 is standard and known in the art. The decanter centrifuge 56 may operate at about 2600 to 3300 RPM. In another example, the range can be 2950 to 3100 RPM. In another example, the range can be 2950 to 3100 RPM. In yet another example, the range can be 2700 to 2950 RPM. In yet another example, the decanter centrifuge 56 may operate at about 3050 RPM. It should noted that different equipment and different equipment size have different RPM ranges and this information is only for exemplary purposes. One such suitable decanter centrifuge 56 is the NX-944HS available from Alfa Laval of Lund, Sweden. In addition, although a single decanter centrifuge 56 is depicted, it should be understood that a plurality of decanter centrifuges 56 may be situated in-line, either in series or parallel, and utilized here. In an alternate embodiment, the decanter centrifuge 56 may be replaced with a standard filter press or rotary vacuum, or other like device, as are known in the art, to dewater the stillage portion.

The centrate from the decanter centrifuge 56 can be joined up with the centrate from decanter centrifuge 54, as shown in FIG. 3, such that at least a portion of the centrate from the decanter centrifuge 56 (along with at least a portion of the centrate from nozzle centrifuge 54) can be recycled back to the nozzle centrifuge 52 to act as the protein counter current wash. And the remainder of the centrate from the decanter centrifuge 56 (along with the remainder of the centrate from nozzle centrifuge 54) may be recycled back to the front end as backset, for example, to the slurry prior to the jet cooking process 14, to the liquefaction step 16, or to the fermentation step 20 for reuse in the dry milling process. As a result of the protein counter current wash, the unfermentable solids content in the combined centrate can be reduced such that fewer unfermentable solids get recycled back into the dry milling process. The centrate may have a dry solids content of about 2.0% to 6.0% compared to a content of about 6.5% in a process without the protein counter current wash. In another example, centrate may have a dry solids content of about 5.9%. This reduction in unfermentable solids in the centrate that is recycled back to the front end of the dry milling process may allow for more corn, or another grain, to be processed at one time. In other words, production throughput can increase as a result of the protein counter current wash. Additional benefits of the protein counter current wash include improved capture efficiency of the nozzle centrifuge 52 and the decanter centrifuges 54, 56 as well as the flexibility to fine tune the protein purity by adjusting the amount of water added to the protein portion before entering the decanter centrifuges 54, 56. Also, a purer protein product and overall protein yield gain can result.

Although not depicted in FIG. 3, it should be appreciated here that the centrate from the decanter centrifuge 56 may be separately piped from the centrate from the decanter centrifuge 54 such that at least a portion of the centrate from the decanter centrifuge 56 can be directly recycled back to the nozzle centrifuge 52 to act as the protein counter current wash and/or the remainder of the centrate from the decanter centrifuge 56 can be directly recycled back to the front end as backset. In addition, it should be appreciated that more than two decanter centrifuges 54, 56 may be provided in sequence here to further dewater the protein portion, as desired.

With further reference to FIG. 3, the dewatered protein portion from the decanter centrifuge 56 can be further optionally dried, such as by being sent to dryer 57, e.g., a spray dryer, ring dryer, flash dryer, compression dryer, or a crystallizer, as is known in the art. In another embodiment, the dewatered protein portion can be subjected to vacuum filtration or other dewatering and drying methods, as are known in the art. The final dried protein portion or product defines a high protein corn meal that may be sold at a much higher price per ton than DDGS or DWGS.

Figure 4:
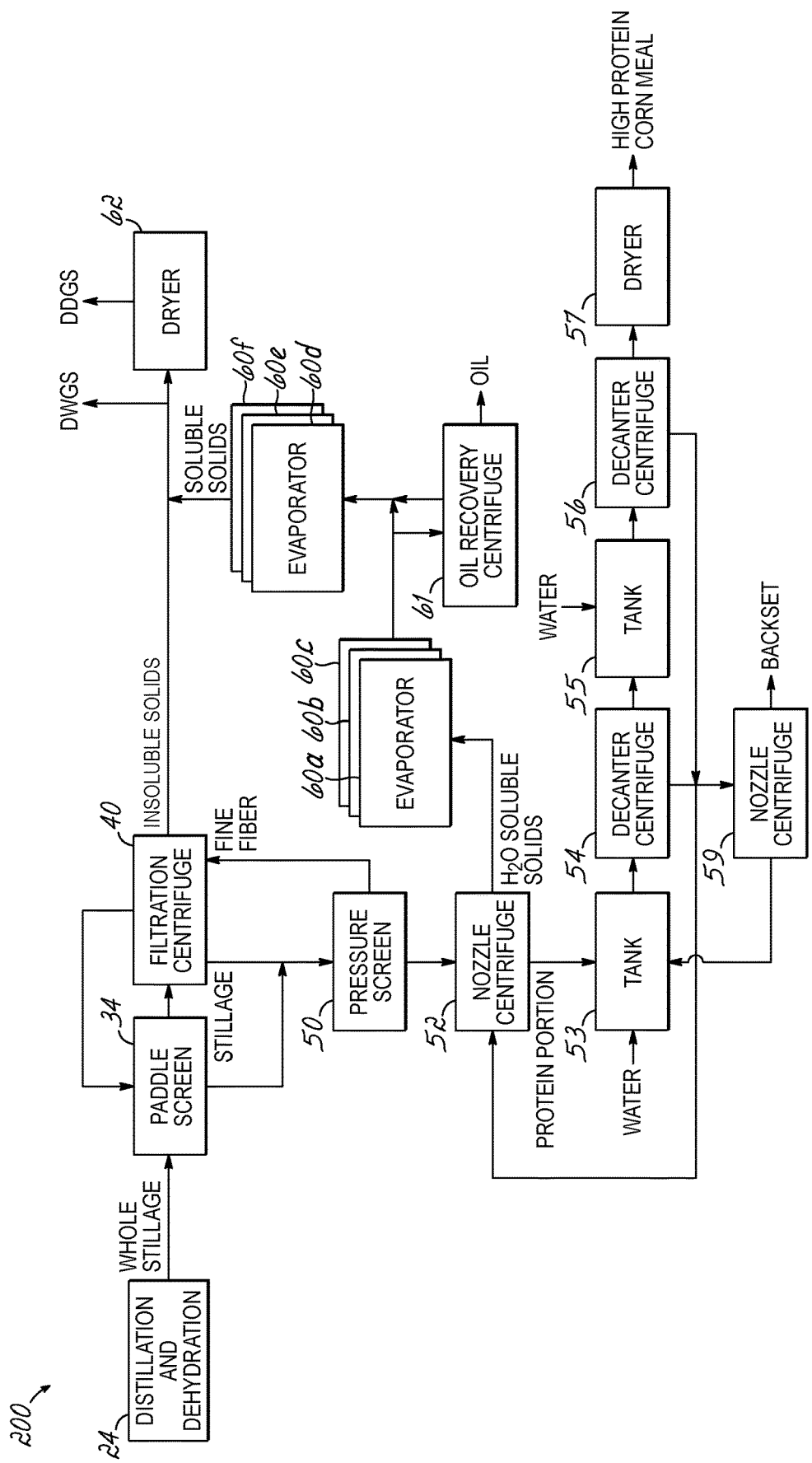
FIG. 4 is a flow diagram of a method and system for reducing the unfermentable solids content in a protein portion in a corn dry milling process for making alcohol and/or other biofuels/biochemicals in accordance with another embodiment of the invention.

In accordance with another embodiment of the invention, FIG. 4 schematically illustrates a method and system, collectively numeral 200, for reducing the unfermentable solids (e.g., carbohydrates) content in a protein portion, via a back end counter current wash, with such protein initially separated with the stillage (centrate) from the whole stillage byproduct produced in a typical corn dry-milling process 10, like that described in FIG. 1. Again, while a typical whole stillage byproduct is utilized here, it should be understood that the whole stillage from any corn (or similar carbohydrate-containing grain) dry milling process may be utilized with the same or similar results.

FIG. 4 is similar to the embodiment of FIG. 3, with the exception that the remainder of the centrate from the decanter centrifuges 54, 56 is sent to and subjected to a nozzle centrifuge 59 to separate the remainder of the centrate into a solids portion, including protein, and a liquid portion, including water soluble solids, instead of being directly utilized as backset. In particular, at the nozzle centrifuge 59, the heavier solids portion, which includes protein, separates from the lighter liquid portion and is removed as the underflow whereas the lighter water soluble solids portion, which includes water soluble solids, can be removed as the overflow.

In one embodiment, the nozzle centrifuge 59 may operate at about 2900 RPM. In another example, the nozzle centrifuge 59 may operate at about 2600 to 3300 RPM. It should be noted that different equipment and different equipment size have different RPM ranges and this information is only for exemplary purposes. One such suitable nozzle centrifuge 59 is the FQC-950 available from Fluid-Quip, Inc. of Springfield, Ohio. In an alternate embodiment, the nozzle centrifuge 59 can be replaced with a standard cyclone apparatus or other like device, as are known in the art. One such suitable cyclone apparatus is the RM-12-688 available from Fluid-Quip, Inc. of Springfield, Ohio. In addition, although a single nozzle centrifuge 59 is depicted, it should be understood that a plurality of nozzle centrifuges 59, either in parallel or series, may be situated in-line and utilized here.

As shown in FIG. 4, the overflow liquid portion may be recycled back to the front end as backset, for example, to liquefaction step 16 or fermentation step 20 for reuse in the dry milling process. The underflow solids portion can sent from the nozzle centrifuge 59 back to storage tank 53 whereat it mixes with the separated protein portion and water. The additional nozzle centrifuge 59 here can increase the amount of protein separated from the stillage portion into the protein portion and help provide a purer protein product and increase overall protein yield. And although not depicted in FIG. 4, it should be appreciated here that the centrate from the decanter centrifuge 56 may be separately piped from the centrate from decanter centrifuge 54 such that the remainder of the centrate from the decanter centrifuge 56 can be directly sent to the nozzle centrifuge 59.

Figure 5:
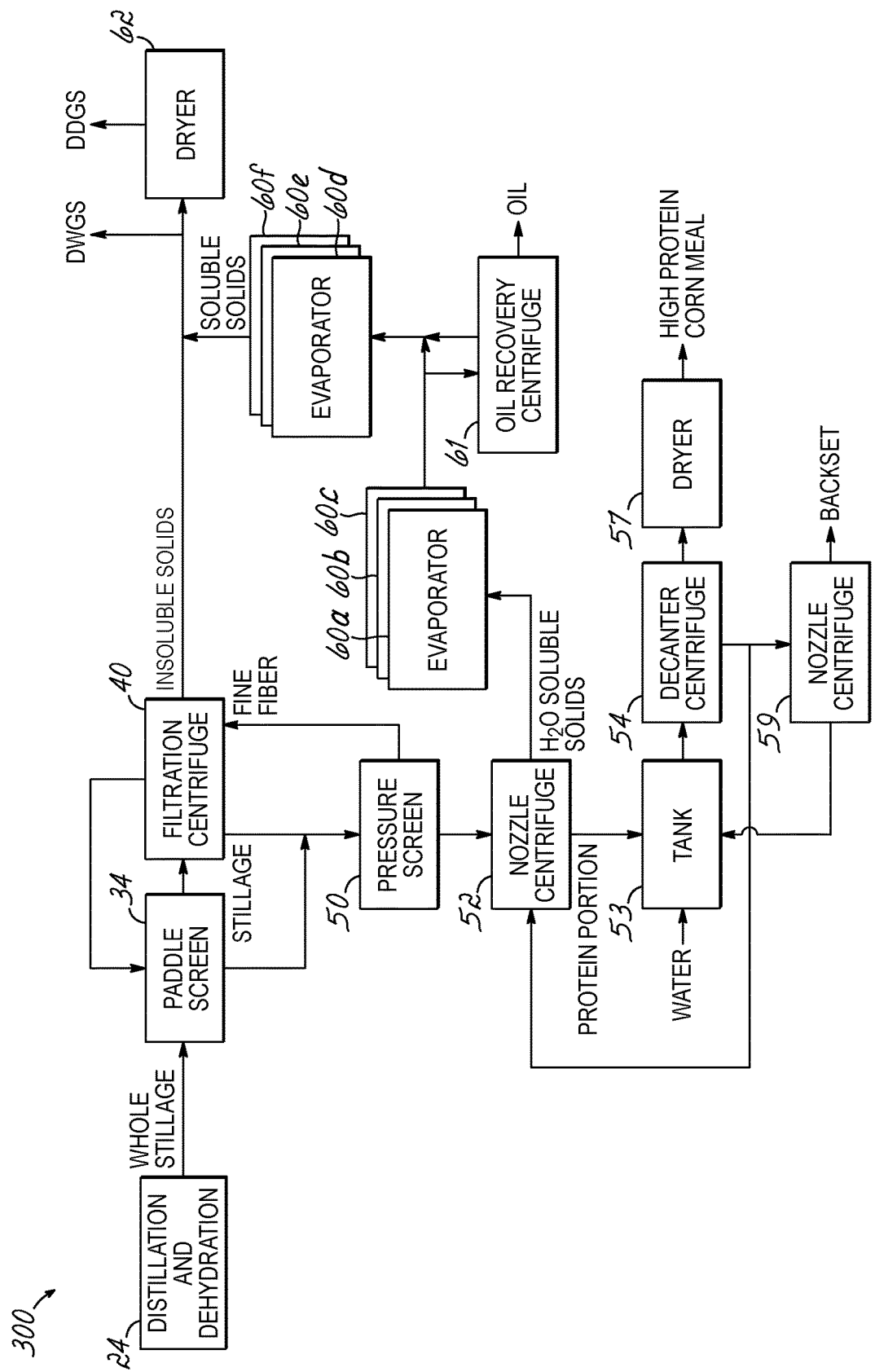
FIG. 5 is a flow diagram of a method and system for reducing the unfermentable solids content in a protein portion in a corn dry milling process for making alcohol and/or other biofuels/biochemicals in accordance with another embodiment of the invention.

In accordance with another embodiment of the invention, FIG. 5 schematically illustrates a method and system, collectively numeral 300, for reducing the unfermentable solids (e.g., carbohydrates) content in a protein portion, via a back end counter current wash, with such protein initially separated with the stillage (centrate) from the whole stillage byproduct produced in a typical corn dry-milling process 10, like that described in FIG. 1. Again, while a typical whole stillage byproduct is utilized here, it should be understood that the whole stillage from any corn (or similar carbohydrate-containing grain) dry milling process may be utilized with the same or similar results.

FIG. 5 is similar to the embodiment of FIG. 4, with the exception that tank 55 and decanter centrifuge 56 have been removed from the method and system 300. Here, the dewatered protein portion from the decanter centrifuge 54 may be further optionally directly dried, such as by being sent to dryer 57, e.g., a spray dryer, ring dryer, flash dryer, compression dryer, or a crystallizer, as discussed above. In another embodiment, the dewatered protein portion can be subjected to vacuum filtration or other dewatering and drying methods, as are known in the art. The final dried protein portion or final product defines a high protein corn meal that may be sold at a much higher price per ton than DDGS or DWGS. In addition, at least a portion of the centrate from the decanter centrifuge 54 can be recycled back to the nozzle centrifuge 52 to act as the protein counter current wash. Here, the water in the protein counter current wash, which was initially provided at tank 53, has already undergone a first wash. The remainder of the centrate from the decanter centrifuge 54 may be sent to and subjected to nozzle centrifuge 59 to separate the remainder of the centrate into a solids portion, including protein, and a liquid portion, including water soluble solids, instead of being directly utilized as backset. At the nozzle centrifuge 59, the heavier solids portion, which includes protein, separates from the lighter liquid portion and is removed as the underflow whereas the lighter water soluble solids portion, which includes water soluble solids, can be removed as the overflow.

With continuing reference to FIG. 5, the overflow liquid portion may be recycled back to the front end as backset, for example, to liquefaction step 16 or fermentation step 20 for reuse in the dry milling process. The underflow solids portion can sent from the nozzle centrifuge 59 back to storage tank 53 whereat it mixes with the separated protein portion and water. The additional nozzle centrifuge 59 again can increase the amount of protein separated from the stillage portion into the protein portion and help provide a purer protein product and increase overall protein yield.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the scope of applicant's general inventive concept.

What is claimed is:

1. A method for reducing an unfermentable solids content in a protein portion at a back end of a starch-containing grain dry milling process for making biofuel and/or a biochemical, the method comprising:
   separating a whole stillage byproduct into an insoluble solids portion, which includes fiber, and a stillage portion, which includes protein;
   adding counter current wash water that is received from a later step in the method to the stillage portion and separating the stillage portion, via weights, into a water soluble solids portion and a protein portion, wherein the addition of the counter current wash water facilitates separation of a larger concentration of unfermentable solids into the water soluble solids portion and wherein the protein portion is not subsequently subjected to an evaporator;
   thereafter, separately adding a first wash water to the separated protein portion followed by dewatering the protein portion to separately provide a centrate portion, which includes first wash water, and a dewatered protein portion that defines a high protein corn meal that includes at least 40 wt % protein on a dry basis, wherein at least a portion of the centrate portion including the first wash water defines at least a portion of the counter current wash water received from the later step in the method; and
   recovering the dewatered protein portion to define the high protein corn meal that includes at least 40 wt % protein on a dry basis, wherein the recovered protein portion remains separate from the whole stillage byproduct.

2. The method of claim 1 further comprising separating the remaining portion of the centrate portion into a solids portion and a liquid portion; and
   combining the solids portion with the wash water that is added to the separated protein portion and utilizing the liquid portion as backset in a step earlier in the method.

3. The method of claim 1 further comprising adding a second wash water to the dewatered protein portion and, thereafter, dewatering the dewatered protein portion to provide a dewatered protein portion that defines the high protein corn meal and another centrate portion defining at least another portion of the counter current wash water.

4. The method of claim 1 wherein the centrate portion defines both a portion of the counter current wash water and a portion of backset that is utilized in a step earlier in the method.

5. The method of claim 1 wherein recovering the protein portion comprises drying the protein portion to define the high protein corn meal.

6. The method of claim 1 wherein prior to any evaporator step, separating the stillage portion, via weights, into a water soluble solids portion and a protein portion.

7. The method of claim 1 further including separating oil from the water soluble solids portion to provide an oil portion.

8. The method of claim 1 wherein the high protein corn meal includes at least 50 wt % protein on a dry basis.

* * * * *